United States Patent [19]

Blomquist et al.

[11] Patent Number: 5,368,562
[45] Date of Patent: Nov. 29, 1994

[54] SYSTEMS AND METHODS FOR OPERATING AMBULATORY MEDICAL DEVICES SUCH AS DRUG DELIVERY DEVICES

[75] Inventors: Michael L. Blomquist, Coon Rapids; Thomas L. Peterson, Shoreview, both of Minn.

[73] Assignee: Pharmacia Deltec, Inc., St. Paul, Minn.

[21] Appl. No.: 100,082

[22] Filed: Jul. 30, 1993

[51] Int. Cl.⁵ .............................................. A61M 5/00
[52] U.S. Cl. ...................................... 604/65; 604/246
[58] Field of Search ........................ 128/DIG. 12, 13; 604/245, 246, 251–255, 151–155, 65, 67

[56] References Cited

U.S. PATENT DOCUMENTS 3,809,871  5/1974  Howard et al. .
4,308,866  1/1982  Jelliffe et al. .
4,320,757  3/1982  hitney et al. .
4,490,798  12/1984 Franks et al. .
4,529,401  7/1985  Leslie et al. .
4,559,038  12/1985 Berg et al. .
4,565,542  1/1986  Berg .
4,578,573  3/1986  Flies et al. .
4,624,661  11/1986 Arimond .
4,650,469  3/1987  Berg et al. .
4,658,371  4/1987  Walsh et al. .
4,676,776  6/1987  Howson .
4,681,563  7/1987  Deckert et al. .
4,722,734  2/1988  Kolln .
4,731,058  3/1988  Doan .
4,741,732  5/1988  Crankshaw et al. .
4,754,401  6/1988  Kaczynski et al. .
4,832,033  5/1989  Maher et al. .
4,889,132  12/1989 Hutcheson et al. .
4,908,017  3/1990  Howson et al. .
4,943,279  7/1990  Samiotes et al. .
5,078,683  1/1992  Sancoff et al. .
5,100,380  3/1992  Epstein et al. .
5,131,816  7/1992  Brown et al. .
5,176,004  1/1993  Gaudet .
5,256,157  10/1993 Samiotes et al. .

FOREIGN PATENT DOCUMENTS 2060151   8/1992  Canada .
0188288   7/1986  European Pat. Off. .
0497041A1 8/1992  European Pat. Off. .
665955A5  6/1988  France .

Primary Examiner—C. Fred Rosenbaum
Assistant Examiner—Manuel Mendez
Attorney, Agent, or Firm—Merchant, Gould, Smith, Edell, Welter & Schmidt

[57] ABSTRACT

An infusion pump system dispenses a drug to a patient in accordance with a predetermined therapy. The system includes a drug delivery system controlled by a microprocessor and replaceable memory modules coupled to the microprocessor for configuring a specific pump user interface and other characteristics required for the therapy. Information specific to a particular patient is entered through input structure on the pump. The memory modules include plural memory sections for storing different types of information.

17 Claims, 2 Drawing Sheets

SYSTEMS AND METHODS FOR OPERATING AMBULATORY MEDICAL DEVICES SUCH AS DRUG DELIVERY DEVICES

FIELD OF THE INVENTION

The present invention relates generally to ambulatory medical devices and methods for operating such devices. In particular, the present invention relates to drug delivery operating systems and methods for operating drug delivery devices.

BACKGROUND OF THE INVENTION

Various ambulatory medical devices are known for treating and/or monitoring patients at a remote site away from the caregiver's office. One example of an ambulatory medical device is a drug delivery device, such as a drug pump, for providing drug delivery to the patient when the patient is away from the caregiver's office.

Certain drugs rarely achieve their maximum therapeutic action through conventional injection techniques. Many drugs reach their full potential only through precise delivery over an extended period of time. With controlled drug infusion through a drug pump, the drug can be given at a precise rate that will keep the drug concentration within the therapeutic margin and out of the toxic range. Ambulatory drug pumps can provide appropriate drug delivery to the patient at a controllable rate which does not require frequent medical attention and which allows the patient to leave the hospital or caregiver's office.

Existing drug pumps are known to include a processor and an imbedded memory device for controlling operation of the pump. In addition, some pumps have various sensors, switches, and devices associated with the pumping operation of the pump.

There is a need for increased sophistication with respect to the drug therapies administered by the drug pumps in order to better treat patients and to reduce health care expenditures by reducing doctor visits and hospital stays.

Controlling operation of the drug pumps in sophisticated therapies is becoming an increasing concern. There is a need for some pumps to be used over a period of time for very different therapies, such as chemotherapy, pain control, nutrition, or antibiotic therapy, for the same or different patients. If the therapy type cannot be changed, or if the therapy type cannot be changed easily, the caregiver must maintain an inventory of pumps with each desired therapy type. Moreover, updates or changes in features of the therapies become a problem if the operating systems of the pumps cannot be changed or if the pumps are not easily changeable. Customization of the pumps is difficult or impossible.

Within each of the broad classes of therapies and other therapies, there are often patient specific parameters which need to be addressed. For example, some desired patient specific parameters may take into account such items as patient weight, and/or the severity of the patient's particular condition. One concern relates to whether and to what extent the pumps can be set for patient specific therapies.

If the pump therapy types and/or the patient specific parameters are changeable, there is a need for these changes to be easy for the caregiver to make. Further, if a problem in the pump operating system develops or if a change in the pump operating system needs to be made when the pump is away from the caregiver's office, this is a further concern.

Also, drug pumps must generally be reliable and durable in the settings in which they are used. Since the pumps are ambulatory, the patient may expose the pump to various environmental conditions and/or impurities that could damage fragile components of the pump. Failure of the drug pump to deliver the appropriate dosage of drug to the patient can be harmful to the patient.

There is a need for operating systems and methods for operating ambulatory medical devices, such as drug pumps, which address at least some of the needs and concerns noted above and other needs and concerns associated with the increasingly sophisticated and complex therapies and devices desired by the health care industry.

SUMMARY OF THE INVENTION

One aspect of the invention relates to an infusion pump system for dispensing a drug to a patient including: a reservoir for holding a drug; a delivery system for delivering the drug to the patient; and a delivery control system for activating the delivery system. The delivery control system includes: a microprocessor for operating the delivery system; a set of memory modules, each module containing information defining a specific user interface; and a coupling arrangement for accepting one of the memory modules. One memory module is coupled to the microprocessor, wherein the microprocessor reads the information and operates the delivery system in conformance with the specific user interface.

The pump system further includes input structure for providing patient specific data and/or other information to the microprocessor. The pump system further includes display structure for displaying output data. An alarm may be provided to alert the patient or caregiver to a problem in the pump system.

The information on the memory modules defines parameters for configuring the pump to mimic a dedicated pump having specific operational characteristics.

A further aspect of the invention relates to an infusion pump system for dispensing a drug to a patient including: a set of memory modules, each memory module containing information defining a specific user interface; a housing with memory access structure for replaceably accepting one of the memory modules; a reservoir mounted on the housing for holding a drug; a drug delivery system for delivering the drug from the reservoir to the patient; and a delivery control system mounted in the housing for operating the drug delivery system. The delivery control system includes a microprocessor coupled to one memory module. The microprocessor receives the information from the memory module to operate the delivery system in conformance with the specific user interface defined by the information in the memory module.

The pump system further includes input structure mounted on the housing for inputting patient specific data to the microprocessor and/or for providing other information to the microprocessor, such as start, stop, or prime command signals for operating the pump system.

The pump system further includes display structure mounted on the housing for displaying output data from the microprocessor. The display structure preferably includes a display panel for displaying operational instructions. The display structure preferably includes an alarm indicator for indicating an abnormal operating condition.

Preferably, each memory module includes a memory type which is non-volatile for storing at least a portion of the specific user interface information. For the program needed to run the pump system, it is preferred in some instances to provide a memory which is only programmed once, or is difficult to erase, reprogram or alter.

One preferred memory module construction includes a plurality of memory sections on the module. A first memory section includes a non-volatile memory such as an EPROM (erasable programmable read only memory) for storing the pump application program information. This type of memory is usually programmed only once, such as at the factory. The pump application program information may for example include at least some of the information needed to operate the drug delivery system in a particular manner, and does not include any patient specific setting information. The remaining information of the pump application program information can reside in memory internal to the pump system, such as internal RAM (random access memory) connected to the microprocessor.

A second memory section on the preferred memory module includes a reprogrammable memory such as RAM for storing the patient specific setting information needed by the pump application program information to operate the drug delivery system and other features of the pump system. The memory module includes a power supply to back up the RAM. The second memory section can be programmed prior to coupling the memory module to the delivery control system from a personal computer or other computer system interconnected to a card interface structure. Also, the second memory section can be programmed from input structure on the pump system after the memory module has been coupled to the delivery control system. The second memory section is also programmable from a personal computer or other computer system located at a local or remote site via a communications port on the pump system when the memory module is coupled to the delivery control system. The second memory section also preferably stores pump event information written to the second memory section by the delivery control system for later usage.

Another aspect of the invention relates to a method of administering a drug to a patient including the steps of: providing an infusion pump system having a reservoir with a drug, a delivery system for delivering the drug to a patient, and a delivery control system including a microprocessor for operating the delivery system, and a set of memory modules, each module containing information defining a specific user interface. A specific memory module is selected, and the specific memory module is coupled to the microprocessor, wherein the microprocessor operates the delivery system in conformance with the specific user interface.

A further aspect of the invention relates to a method of operating an infusion pump including the step of providing a memory module with a plurality of memory sections, and programming a first section with pump application program information, and programming a second section with patient specific setting information. The memory module is coupled to a pump control system for operating a delivery system interconnected to a fluid reservoir. The second memory section is programmed either before coupling the memory module to the control system via an external computer system, or after coupling via input structure associated the pump. The second memory section is also programmable after coupling to the control system via an external computer system. The method further preferably includes programming the second section with pump event information from the control system.

BRIEF DESCRIPTION OF THE DRAWINGS

In the drawings, where like numerals refer to like features throughout the several views.

DETAILED DESCRIPTION OF THE PREFERRED EMBODIMENT

Figure 1:
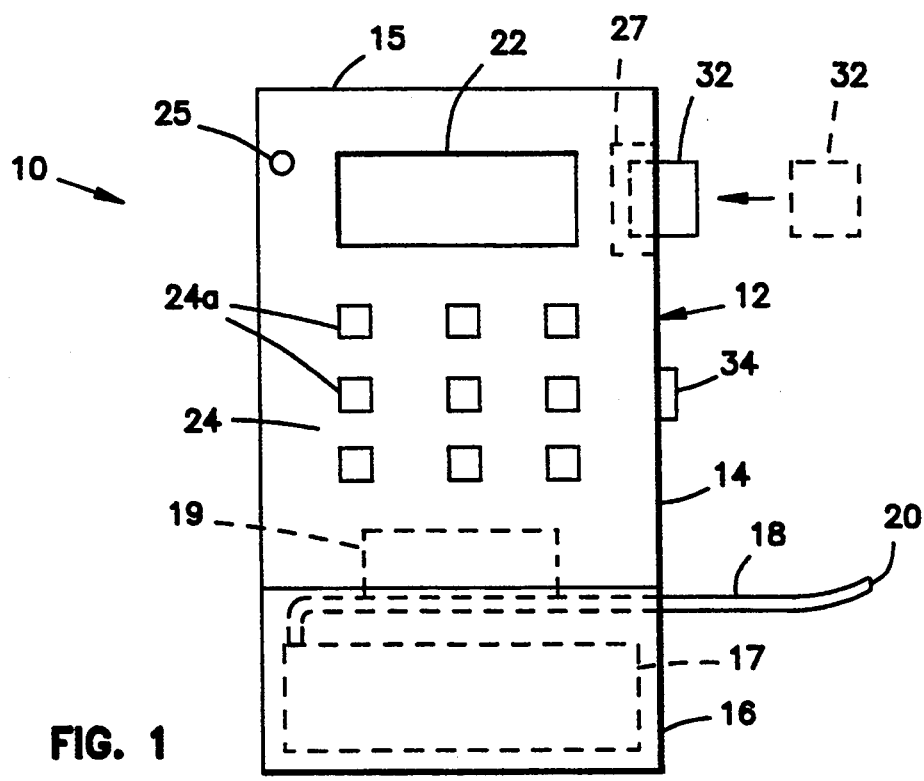
FIG. 1 is a schematic diagram of a drug pump according to the present invention.

Referring now to FIG. 1, a system 10 for operation of pump 12 is shown. Pump 12 includes a control module 14 and a replaceable cassette 16 mounted thereto. Cassette 16 provides a reservoir 17 for holding the drug or other fluid to be pumped to the patient. Cassette 16 may include the fluid reservoir 17 in an interior of cassette 16, as shown in FIG. 1. Alternatively, cassette 16 may include a conduit linking cassette 16 to a remote container of fluid (not shown).

Control module 14 includes an outer housing 15 and a pumping mechanism 19 for delivering fluid from the fluid reservoir of cassette 16 through a tube or conduit 18 to a patient. An example of a pumping mechanism 19 is shown in U.S. Pat. No. 4,559,038, the disclosure of which is incorporated herein by reference. In U.S. Pat. No. 4,559,038, the pumping mechanism includes a rotatable cam shaft which engages a reciprocating inlet valve, a reciprocating expulser, and a reciprocating outlet valve. The valves and expulser engage the tube 18 associated with cassette 16. The rotating camshaft moves the valves and expulser to pump fluid through the tube 18 to the patient. Other pumping mechanisms are anticipated for pumping fluid to the patient, including a syringe pump in which a pumping mechanism drives the plunger of a syringe to pump the fluid in the syringe to the patient. In that case, the end of the syringe is connected to the patient. Still other pumping mechanisms are anticipated such as rotary peristaltic, and wave style mechanisms with a plurality of fingers to pump fluid in the conduit as the fingers sequentially engage the conduit.

Tube 18 extends from pump 12 and terminates at a patient end 20. Fluid flows from the fluid reservoir 17 of cassette 16, past the pumping mechanism 19 of control module 14, and through tube 18. Patient end 20 can be interconnected to a patient intravenously.

Control module 14 of pump 12 includes a control system 21 for activating the pumping mechanism 19 to deliver the drug or other fluid to the patient at the desired time. The control system 21 also preferably: controls a display 22, such as an LCD-type (liquid crystal display) display; receives inputs from a keyboard 24; controls a visual or audible alarm 25; and electronically transmits and receives information through an input-/output communications port 34. Keyboard 24 includes at least one key or button. Keyboard 24 in FIG. 1 is shown to include a plurality of individual keys 24a. The control system 21 also preferably controls one or more switches, sensors, or devices associated with the operation of pump 12. The switches, sensors, and/or devices of pump 12 may includes an occlusion detector, a cassette latch/lock sensor, a temperature sensor, a cassette identification device, and/or other device(s). These switches, sensors, or devices are represented generally as pump device 23 in FIG. 2.

As will be discussed in more detail below, the control system 21 includes a microprocessor 28 for controlling operation of the pump mechanism 19. The microprocessor 28 is coupled to an internal memory 30 and a removable memory module 32. Internal memory 30 is located in control module 14 and is preferably nonremovable. In some cases, a removable wired in internal memory 30 is desired. Internal memory 30 is preferably EPROM for use by microprocessor 28 and holds appropriate memory for the pump 12. Other memory types are anticipated instead of EPROM, depending on the needs of the caregiver.

Removable memory module 32 is selectively connectable to and disconnectable from control module 14 via a module interface 27 mounted to control module 14. Module interface 27 electrically interconnects memory module 32 to microprocessor 28. As an example, memory module 32 may be a card or cartridge construction, such as a credit card-sized card (approximate length and width, and somewhat thicker than a conventional credit card) containing an appropriate memory device or devices for storage of information used to run/operate pump 12. Memory module 32 may contain a plurality of connector sockets at one end for interfacing with a plurality of connector pins in module interface 27 of pump 12. The connector sockets are linked to the memory device(s) on memory module 32.

Memory module 32 is a portable memory unit which is used to configure the pump 20 in a desired manner. Memory module 32 defines those parameters needed for configuring the pump 12 to mimic a dedicated pump having specific operational characteristics. The information programmed into internal memory 30 is dependent on the information within memory module 32. In this regard, memory module 32 must be connected to the microprocessor 28 of the pump 12 in order for the pump to operate in the preferred operating system. Once the two are connected via module interface 27, the microprocessor 28 reads the information from memory module 32 and delivers the drug in conformance with the specific user interface contained on the memory module 32.

The preferred pump operating system includes a plurality of memory modules 32, each having different information programmed on the respective memory module. In this manner, the characteristics of the pump can be varied by selecting an appropriate memory module 32. Memory module 32 includes a specific user interface programmed onto the memory of the module to define a pumping function of pump 12 that will operate or permit operation of pumping mechanism 19 in a particular and desired manner. Memory module 32 includes at least some of the information needed by the microprocessor 28 to operate the pump 12 such as to deliver fluid to the patient. At a minimum, the internal memory 30 needs appropriate programming to instruct microprocessor 28 to read information from the memory module 32 interconnected to pump 12 at interface 27. In some cases, internal memory 30 can include other information needed by microprocessor 28 in all or in several of the different configurations of pump 12 desired by the caregiver. In other words, memory module 32 can, but does not need to, contain all information needed by microprocessor 28 to run pump 12 except the information needed by microprocessor 28 to read from interface 27. The patient specific setting information can be preprogrammed onto memory module 32 or the information can be added later via communications port 34 or keyboard 24.

It is also preferred, but not required, that internal memory 30 include appropriate programming so that if memory module 32 is pulled from module interface 27, pump 12 interrupts the pumping operation and sends an appropriate signal or message to alarm 25 or display 22. The interrupt program on internal memory 30 can be initiated by a signal received by microprocessor 28 from a suitable sensor that senses when memory module 32 is no longer connected to module interface 27.

Figure 5:
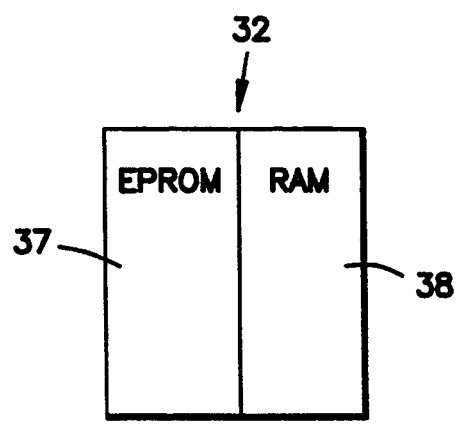
FIG. 5 is a schematic diagram of a memory module according to the present invention.

Memory module 32 itself preferably contains a plurality of memory sections. Preferably, each memory module 32 includes a section of non-volatile memory, such as EPROM (erasable programmable read only memory) or ROM (read only memory), for storing at least a portion of the specific user interface information. FIG. 5 shows a memory module 32 which contains at least two types of memory. A first memory section 37 includes non-volatile memory, such as an EPROM, for storing the pump application program information. The pump application program information may include for example at least some of the information needed to operate elements of the control system 21 in a particular manner, but preferably does not include any patient specific setting information. For example, all the executable code needed to run pumping mechanism 19 to deliver the appropriate therapy may be stored in first section 37.

The EPROM of the first section 37 is preferably programmed at the factory or by a programming unit such as a personal computer or other computer system, and it is difficult, although not impossible to reprogram if desired by the caregiver. Thus, it is a safe way to store data that does not change. Most of the data used to customize the pump for a specific application is preferably stored in EPROM. Although the non-volatile section 37 of the memory modules 32 are described as EPROM, it will be appreciated that other forms of memory may be used, such as ROM, and one-time programmable EPROM. In some applications, flash memory may be desirable. If flash memory is provided, typically there is some safeguard provided such that first section 37 is not inadvertently erased or reprogrammed, such as requiring special programming in order to reprogram the flash memory, or requiring a larger power supply to reprogram than is otherwise usually available with respect to pump 12.

Information stored in the non-volatile section 37 of memory module 32 specifies the particular operational mode or application of the pump 12, including, but not limited to continuous infusion, PCA (Patient Controlled Analgesia) infusion, intermittent infusion, real time infusion, fixed multiple step infusion, and complex combination infusion. These infusions can be used for various therapies including chemotherapy, antibiotic therapy, nutrition therapy, and pain control therapy, and other therapies.

The EPROM of the memory module 32 may also be configured as a non-delivery module for performing calibration and/or maintenance functions of pump 12. The purpose of this type of module is to provide an interactive calibration and/or maintenance function that allows a complete and thorough check of the pump 12 and then documents the results of the check.

Information stored in the pump 12 after it leaves the factory may preferably be stored in a second memory section 38 of replaceable memory module 32. The second memory section 38 is reprogrammable such as RAM (random access memory), which can be written to and read from as many times as desired. As a result of using this type of memory, memory module 32 is also provided with a power supply to back up the RAM when the module 32 is disconnected from the pump 12. Battery backed up RAM is useful to hold information on memory module 32 after disconnection from pump 12 to save the information written to the second memory section 38 of memory module 32 in the event the memory module 32 inadvertently becomes disconnected from pump 12, or in the event a disconnection is needed with a subsequent connection to the same pump or a different pump. Information stored in the second memory section 38 can be read from another pump or computer system interconnected to the module 32 without the presence of pump 12.

The second memory section 38 of memory module 32 is useful for storing patient specific setting information. Preferably, the second memory section 38 is also used for storing pump event information that is generated as the pump operates and written to memory module 32 for storage. It is preferred that only those delivery parameters which are identified by the specific operational mode configured into the non-volatile first memory section 37 of memory module 32 be programmable to memory module 32 when memory module 32 is inserted into the pump 12. In that preferred situation, no other delivery parameters can be entered, and characteristics which have been factory/programming unit set are not allowed to be changed. RAM type memory for the second memory section 38 is useful due to its ability to be reprogrammed easily and a large number times.

Figure 2:
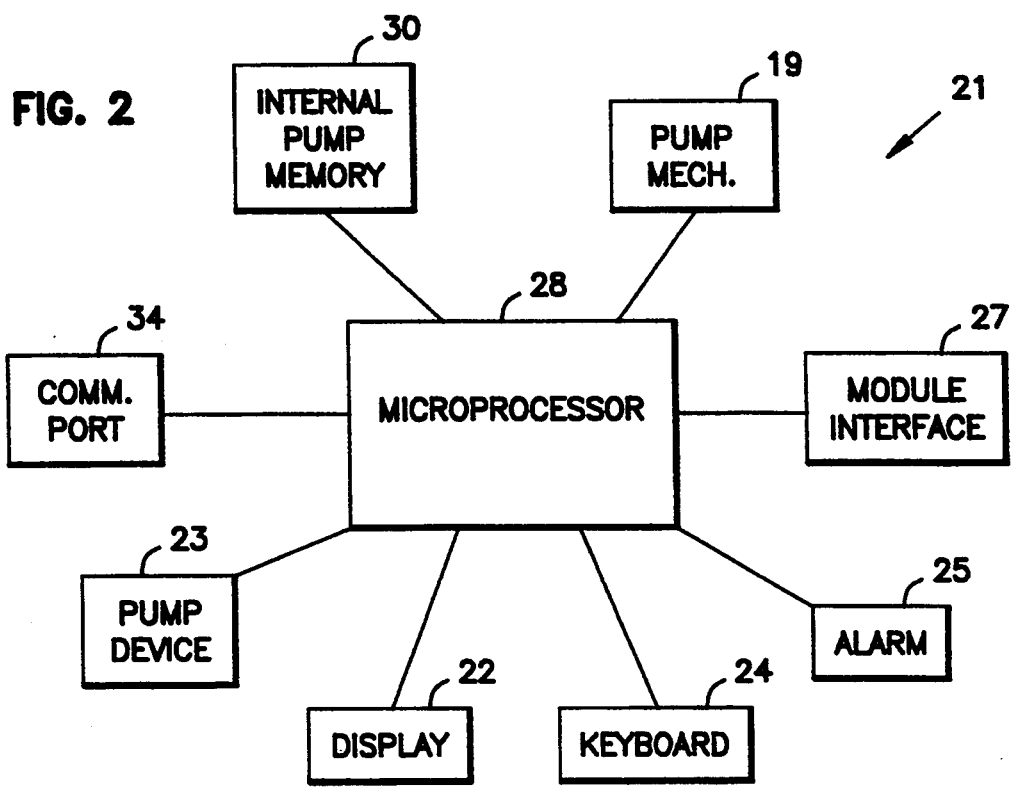
FIG. 2 shows a block diagram of a control system for the pump shown in FIG. 1.
Figure 4:
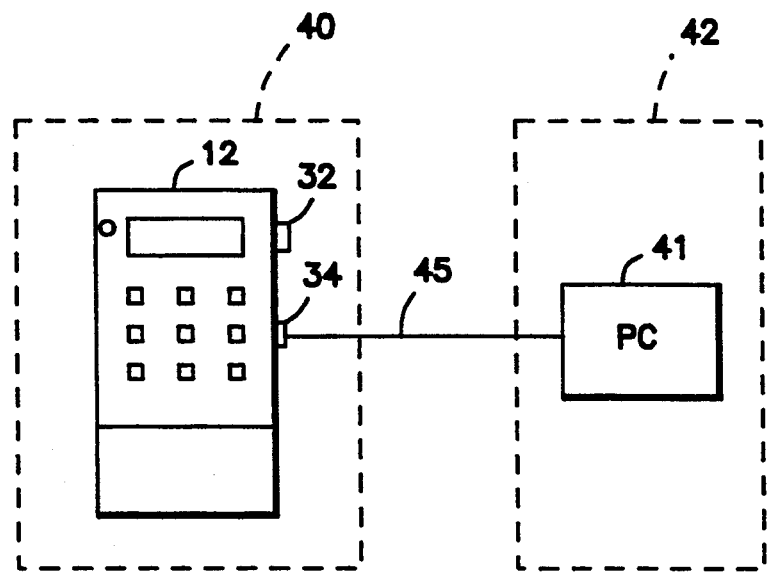
FIG. 4 is a schematic diagram illustrating the pump of FIG. 1 linked to a personal computer located at a remote site.

The second memory section 38 of memory module 32 may be programmed in several ways. As shown in FIGS. 1 and 2, the pump 12 is provided with a communications port 34. The communications port 34 allows for the programming of the pump 12 via a personal computer or other computer system 41 interconnected to the pump 12, as shown in FIG. 4. The second memory section 38 of memory module 32 may be programmed remotely or locally via the communications port 34 on the pump 12 when memory module 32 is coupled to the microprocessor 28 of the pump. In this manner, information can be written to the second memory section 38 of memory module 32 from a computer system 41 located at a remote site 42, different from site 40 where pump 12 is located, as shown in FIG. 4. Communications link 45 between pump 12 and computer system 41 includes modem links with conventional telephone lines, cellular phone systems, fiber optics links, satellite links, microwave links, or other remote links. Alternatively, pump 12 can be programmed when pump 12 and computer system 41 are located at the same site. In addition, information can be sent from memory module 32 to computer system 41 via communications port 34, such as to view information programmed on memory module 32 or to download information from memory module 32 for generating reports, for example.

Figure 3:
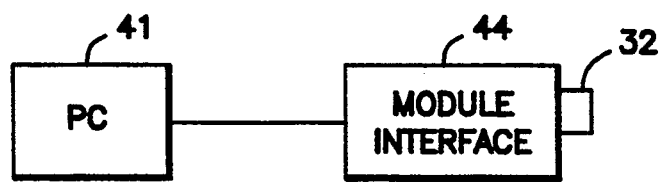
FIG. 3 is a schematic diagram of a memory module linked to a personal computer.

The second memory section 38 of memory module 32 also allows for programming or reprogramming of the memory module 32 itself, prior to coupling memory module 32 to the microprocessor 28 of the pump, as shown in FIG. 3, via a personal computer or other computer system 41 linked to memory module 32 through a module interface device 44. In addition, information can be sent from memory module 32 to computer system 43 in a similar manner.

If the appropriate programming devices and/or programming is provided, the first memory section 37 can be programmed or reprogrammed (if possible given the memory selected) via PC 41 in either a system as shown in FIGS. 3 or 4.

The communications port 34 allows a personal computer (PC) 41 to read the data stored in memory module 32, as well as to write to the second memory section 38 of memory module 32. Preferably, standard functions of the memory module 32 can be programmable via a PC. Other functions which can be input into the memory module 32 via a PC include but are not limited to patient history information, such as patient name, age, weight, sex, and chart number; emergency information; insurance information; and calibration/maintenance information. Preferably, the user is not able to alter this data from the keyboard 24. A PC interface is required to enter new data of this type, although such a feature is optional.

One type of data that can be stored in the second memory section 38 of memory module 32 is a drug delivery program or patient specific setting information. This data can be entered into the pump through manual keyboard entry of keyboard 24, or a PC 41. The drug delivery program shall be retained by second memory section 38 of memory module 32 if the pump 12 loses power or if memory module 32 is removed from the pump. This retained drug delivery program shall remain in memory module 32 until it is either rewritten or erased from the memory module. When changes have been made to the operating parameters of the pump, those changes shall be logged so that a history of drug delivery profile changes may be retained. In addition, the drug delivery program can be changed by data input to the pump via the keyboard 24 or PC or other programming unit and shall automatically become the operating program of the pump it is used with.

Another type of data that can be stored in the second memory section 38 of memory module 32 is drug delivery history including pump event information. This history may include such information as the amount of drug delivered, the number of PCA doses attempted and given, and changes to the operating parameters and flow profiles. In this manner, memory module 32 can be used as a medication administration log for verifying compliance, titrating medication, and record keeping. Removal of memory module 32 from the pump, however, shall not cause the retained information to be lost. Memory module 32 is also capable of retaining extended delivery history information written into the memory module 32 via a programming unit. The pump 12, however, cannot change this information.

Unlike the characteristics which have been factory set, the drug delivery program, drug delivery history information, or extended delivery history information retained within memory module 32 can either be displayed on the LCD display 22, printed out via an external printer (not shown), or stored for future recall.

Although the memory modules are described to include EPROM and RAM, it will be appreciated that other types of memory may be added, such as EEPROM (electrically erasable programmable read only memory), to back-up the RAM and/or to store information not easily restored and not stored in first section 37 of memory module 32. For example, the EEPROM may be useful for storing a module or a pump serial number, error code history regarding pump operation errors, and/or pump or module usage counter data. During use, it may be desireable to erase and reprogram such information periodically. The RAM may be too volatile for the information, if for example the battery back up is removed or changed.

As previously mentioned, the control system may also include a communications port 34 capable of interfacing with peripheral equipment and accessories, such as a personal computer or printer. The communications port 34 is preferably a standard RS232 communications port. Information programmed into memory module 32 instructs information to be transmitted or received via the communications port 34. This feature allows information being received via the communications port 34 to control the pump 12. This feature also allows for the downloading of any or all of the memory modules's data to a printer, a personal computer, or other RS232-compatible equipment.

It is preferred, although not required, that text commands in the operating program for display 22 be stored in first memory section 37 of memory module 32. In this manner, changes in the language (for example, English to Spanish) displayed on display 22 can be easily changed by selecting an appropriately programmed memory module 32 or programming memory module 32 to include the desired language for the displayed text. Alternatively, memory module 32 can be programmed to display bilingual text on display 22, for example.

As shown in FIG. 1, the control module 14 has interface 27 accessible from the outside of housing 15 for holding memory module 32 so that it is readily removable and replaceable with the same or another memory module. The interface to memory module 32 shall be buffered in such a way that the microprocessor 28 will not lock up when memory module 32 has a defect. However, the microprocessor 28 may be configured to determine if memory module 32 is properly attached.

The general operation of the infusion pump shall now be described. Initially, a memory module 32 corresponding to a specific delivery profile is inserted into module interface 27. In other words, a memory module 32 is provided for a specific user interface, thereby defining the characteristics of a dedicated pump. The pump is not operational in a pumping mode without a memory module properly installed. The microprocessor 28 reads the information from memory module 32. The pump is then characterized as being in a particular type of operational mode, such as PCA, continuous, intermittent, or maintenance/calibration.

The microprocessor 28 reads any patient specific setting information from the second section 38 of the memory module 32 and then, if necessary, provides operational instructions on the LCD display 22 and, if necessary, requests any needed patient specific setting information. Display 22 is usable to request dosing inputs such as flow rate, dose size, patient weight, drug concentration, etc., as required. The display 22 may also be used to identify the type of memory module 32 inserted in module interface 27, and other initial information, so as to insure that the pump is operated properly and that the patient will receive the correct drug dose. The operator of the pump enters any requested information through the keyboard 24. Menu driven data entry procedures may be utilized. The keys 24a may be dedicated to pump functions, such as starting or stopping the pump.

Once the requested information is entered, the microprocessor 28 adjusts the operational parameters for the pump to meet the requirements of the specific patient, and on command starts delivery the drug. The microprocessor 28 monitors the operation of the pump on a continuous basis, and in case of a malfunction, it activates alarm 25 and may cease pumping in the appropriate situation. If a different application is needed at a later date, or if a problem or update in the application develops, module 32 is removed and replaced with a new module 32. If a pump function besides pump mechanism 19 is to be operated in a different manner or if a maintenance or calibration function is desired, module 32 is conveniently removed and replaced with the appropriate new module 32. If control module 14 needs servicing or replacing, module 32 can be removed from control module 14 and reinserted into the same control module 14 at a later time or a different control module 14 without a loss of information needed to pump fluid to the patient.

One advantage of using removable memory modules 32 is that standard control modules 14 and cassettes 16 can be manufactured by pump manufacturers, and custom pumps can then be easily supplied to each pump supplier/caregiver in the desired configuration(s) by supplying appropriately programmed memory modules 32. For example, some caregivers may desire certain messages displayed on display 22, or that certain ranges be broader or narrower with respect to acceptable patient specific setting information. Such customization is conveniently handled by supplying the caregiver with the appropriate memory modules 32.

The foregoing constitutes a description of various preferred embodiments. Numerous changes to the preferred embodiments are possible without departing from the spirit and scope of the invention. Hence, the scope of the invention should be determined with reference not to the preferred embodiments, but to the following claims.

What is claimed is:

1. An infusion pump system for dispensing a drug to a patient comprising:
   a. reservoir means for holding a drug;
   b. delivery means for delivering said drug to said patient;
   c. delivery control means for activating said delivery means, said delivery control means including:
      (i) microprocessor means for operating said delivery means;
      (ii) a set of memory modules, each module containing information defining a specific user interface, wherein each memory module includes a plurality of sections of memory, a first section of memory comprising a non-volatile memory, and a second section comprising an electrically reprogrammable memory; and (iii) coupling means for accepting one of said memory modules, and coupling said one memory module to said microprocessor means, wherein said microprocessor means reads said information and operates said delivery means in conformance with said specific user interface.

2. The system of claim 1 further comprising input means for providing patient specific data to said microprocessor means.

3. The system of claim 1, further comprising display means for displaying output data.

4. The system of claim 1, wherein said information defines parameters for configuring said pump to mimic a dedicated pump having specific operational characteristics.

5. The system of claim 1, wherein said first section comprises EPROM and said second section comprises a battery backed up RAM.

6. An infusion pump system for dispensing a drug to a patient, said system comprising:
   a. a set of memory modules, each memory module containing information defining a specific user interface, wherein each memory module includes a plurality of sections of memory, a first section of memory comprising a non-volatile memory, and a second section comprising an electrically reprogrammable memory;
   b. a housing with memory access means for replaceably accepting one of said memory modules;
   c. reservoir means mounted on said housing for holding a drug;
   d. drug delivery means for delivering said drug from said reservoir to said patient; and
   e. delivery control means mounted in said housing for operating said drug delivery means, said delivery control means including microprocessor means coupled to said one memory module, said microprocessor means receiving said information from said one memory module to operate said delivery means in conformance with the specific user interface defined by the information in said one memory module.

7. The system of claim 6 further comprising input means mounted on said housing for imputing patient specific data to said microprocessor means.

8. The system of claim 6, further comprising display means mounted on said housing for displaying output data from said microprocessor.

9. The system of claim 8, wherein said display means includes a display panel for displaying operational instructions.

10. The system of claim 8 wherein said display means includes an alarm indicator for indicating an abnormal operating condition.

11. The system of claim 10, further comprising input means mounted on said housing for inputting information to said microprocessor.

12. The system of claim 6, wherein said first section comprises EPROM and said second section comprises a battery backed up RAM.

13. The system of claim 6, wherein said first section stores pump application program information and said second section stores patient specific setting information.

14. A method of administering a drug to a patient comprising the steps of:
   a. providing an infusion pump system having a reservoir with a drug, a delivery means for delivering said drug to a patient, and a delivery control means including a microprocessor for operating said delivery means, and a set of memory modules, each module containing information defining a specific user interface, wherein said specific user interface includes pump application program information, said pump application program information being preprogrammed onto said specific memory module in a first non-volatile memory section, and wherein patient specific setting information is programmable onto said specific memory module in a second electrically reprogrammable memory section;
   b. selecting a specific memory module;
   c. coupling said specific memory module to said microprocessor, wherein said microprocessor operates said delivery means in conformance with said specific user interface; and
   d. programming said patient specific setting information onto said specific memory module from input means associated with said delivery control means for inputting information to said delivery control means.

15. The method of claim 14, further comprising the steps of: generating pump event information at said delivery control means, and programming said pump event information onto said specific memory module.

16. A method of operating a pump comprising the steps of:
   a. providing a memory module having a plurality of different memory sections;
   b. programming a first section with pump application program information;
   c. programming a second section with patient specific setting information; and
   d. coupling the memory module to a microprocessor of a pump.

17. The method of claim 16, wherein, prior to coupling the memory module to the pump, the memory module is coupled to a computer system for carrying out the step of programming the first section of memory, and wherein, subsequent to coupling the memory module to the pump, the step of programming the second section of memory is carried out through input means on the pump for inputting information to the pump.

* * * * *